(12) United States Patent
Zucca et al.

(10) Patent No.: US 8,127,804 B2
(45) Date of Patent: Mar. 6, 2012

(54) DEVICE AND METHOD FOR THE DILUTION AND PREPARATION OF ANTIBLASTIC DRUGS

(75) Inventors: Giuseppe Zucca, Quartucciu (IT); Michele Desogus, Cagliari (IT); Maria Cristina Deidda, Quartucciu (IT)

(73) Assignee: Bioduct S.R.L., Cagliari (IT)

( * ) Notice: Subject to any disclaimer, the term of this patent is extended or adjusted under 35 U.S.C. 154(b) by 640 days.

(21) Appl. No.: 12/294,106

(22) PCT Filed: Aug. 4, 2006

(86) PCT No.: PCT/IB2006/002134
§ 371 (c)(1),
(2), (4) Date: Nov. 18, 2008

(87) PCT Pub. No.: WO2007/110684
PCT Pub. Date: Oct. 4, 2007

(65) Prior Publication Data
US 2009/0165886 A1    Jul. 2, 2009

(30) Foreign Application Priority Data
Mar. 24, 2006  (IT) .............................. MO2006A0097

(51) Int. Cl.
*B65B 1/04*  (2006.01)

(52) U.S. Cl. ............................................. 141/9; 141/27
(58) Field of Classification Search ................ 141/9, 27, 141/82, 94, 285.5, 309; 435/404, 289.1
See application file for complete search history.

(56) References Cited

U.S. PATENT DOCUMENTS

| | | | |
|---|---|---|---|
| 3,404,839 A * | 10/1968 | Pipkins et al. ................ | 239/113 |
| 4,587,793 A | 5/1986 | Brennan et al. | |
| 5,037,390 A | 8/1991 | Raines et al. | |
| 7,361,739 B2 * | 4/2008 | Bellotti et al. ................ | 530/359 |
| 2005/0090444 A1 | 4/2005 | Bellotti et al. | |
| 2005/0277912 A1 | 12/2005 | John | |
| 2005/0278066 A1 | 12/2005 | Graves et al. | |

FOREIGN PATENT DOCUMENTS
EP        1 563 819 A1      8/2005

OTHER PUBLICATIONS
International Search Report for PCT/IB2006/002134, mailed Dec. 15, 2006.
International Preliminary Report on Patentability with 8 Amended Sheets, dated Jun. 16, 2008.
Official Action dated Nov. 8, 2011, issued in Israeli Patent Application No. 194,276, (2 pages).

* cited by examiner

*Primary Examiner* — Davis Hwu
(74) *Attorney, Agent, or Firm* — Nixon & Vanderhye P.C.

(57) ABSTRACT

A device and a method for the dilution and preparation of antiballistic drugs, the device comprises a drug preparation unit connected to a controlling device; the drug preparation unit comprises a first central tank, in which there is a solvent, typically a physiological and/or glucosate solution, a first positive-displacement pump, an emptying unit connected to a positioning and locking arrangement provided with a housing suitable for receiving various dimensions and formats of dimensions and formats of bottles of drug; the first positive-displacement pump transfers in a dosed manner the solvent from the central tank to the bottle, and in succession from the bottle to a further tank of semifinished drug; the diluted drug solution in the further tank is then transferred to a container of prepared drug in a determined quantity for infusion into a patient.

28 Claims, 8 Drawing Sheets

DEVICE AND METHOD FOR THE DILUTION AND PREPARATION OF ANTIBLASTIC DRUGS

CROSS-REFERENCE TO RELATED APPLICATIONS

This application is the U.S. national phase of International Application No. PCT/IB2006/002134, filed 4 Aug. 2006, which designated the U.S. and claims priority to Italy Application No. MO2006A000097, filed 24 Mar. 2006, the entire contents of each application is hereby incorporated by reference.

DESCRIPTION

The invention relates to a device for the dilution and preparation of antiblastic drugs, i.e. drugs with an antineoplastic effect.

In the prior art, antiblastic drugs are diluted and prepared by specialised operators within facilities called A.D.U.s (Antiblastic Drugs Units) and A.D.U.H.s (Antiblastic Drugs Units and Handling), which should always be present in all oncological departments that administer antiblastic treatments.

In fact, handling antiblastic drugs requires particular precautions on the part of operators inasmuch as the contact, the absorption or any other form of contamination by these drugs can have toxic and cancerogenous effects on the operators. Even if these harmful effects have not actually been scientifically proven it is nevertheless necessary to follow guidelines for safe and correct handling of these drugs.

Furthermore, as antiblastic drugs are supplied by the manufacturers in conditions of sterility, such conditions have to be maintained during all the handling and administration steps, following the good practice guide of the official pharmacopoea.

The operator in charge of the dilution and the preparation of the antiblastic drugs receives from a doctor the treatment plan, which has to be customised for each single patient: customisation has to take account of the standard doses of the chemotherapeutical protocols and of the bodily surface of the patient.

The chemotherapeutical protocols are generally constituted by several antiblastic drugs (polychemotherapy), each of which will be reconstituted in a single bottle and never be mixed with the other bottles.

The dilution of a lyophilised or liquid drug with the solvent (typically a physiological or glucosate solution), is the responsibility of a specialised nurse, who has to be provided with personal protective equipment (PPE) and has to operate inside a preparation room provided with safety booths with vertical laminar flow hoods with double air-emission filters, as illustrated in FIG. 1.

Maintenance of the safety cabins with vertical laminar flow hoods always has to be thorough: decontamination is conducted regularly by the operators.

In the preparation room there are stored the personal protective equipment (PPE) and the safety arrangement to be used in the event of emergencies due to acute exposure of the skin or of the eyes.

Operators who wear personal protective equipment (PPE) whilst working cannot moreover have contact with other people, cannot consume food or drink and have to follow strictly a series of precautions.

The personal protective equipment (PPE) provided is all disposable: overalls in nonwoven fabrics (NWF) and non-talc gloves—talc gloves in fact leave traces on the hands and on the equipment that may absorb the drugs.

The personal protective equipment (PPE) is used double and has to be changed after every 30 minutes in contact with the drugs. The operators also have to wear masks, caps and footwear; the masks do not prevent the absorption of the drugs by the operators, but are obligatory for aseptic preparations, as are the caps and footwear.

In order to inject the correct dose of drug into the container with the solution, syringes and infusion tubing that have special fittings, for example Luer-Lock-type fittings, to prevent the needle becoming disconnected are used.

Each bottle of the treatment is labelled with the name of the intended patient, the name of the drug and the quantity of drug that it contains. As a treatment, premedication plan and chemotherapeutical protocol always require more than a drug, it is advisable to number the bottles with the various drugs in the order of the indicated administration sequence. Furthermore, the container with the drug has to be protected from exposure to light to prevent the drug deteriorating.

Once the drugs have been prepared in the required sequence and dosage, the drugs can be administered to the patient endovenously by connecting the bottle with a suitable arrangement for infusion into the patient, for example a cannula needle inserted into the vein, or a tunnelised central venous catheter (abbreviated to CVC), or a Port-Cat.

For conveying, packaging and storage of the preparations bottles and devices in plastics and not in glass are used.

Also the other operators (professional nurses, auxiliary departmental staff) who may come into contact with biological substances of patients undergoing treatment have to wear the personal protective equipment (PPE), and are subject to six-monthly check-ups.

From the foregoing remarks it is clear that the dilution and preparation of the antiblastic drugs is rather long, laborious and also subject to the possibility of errors and contamination.

Apparatuses have therefore been proposed to facilitate the dilution and preparation of the antiblastic and/or chemotherapeutical drugs.

In the German patent DE-43 14 090 C2 a kit is presented, preferably a disposable kit, for the preparation of a solution of a medicine supplied in solid state to be administered through a catheter, for example for endovascular chemotherapy of cancer of the bladder.

The kit comprises a container in which a solvent is stored for the dilution of the solid drug; a receptacle for the diluted drug and a connecting element between the container and the receptacle with an actuatable passage valve and a connection through which the prepared solution can be supplied to a catheter and similar.

The kit comprises a container, a receptacle and a connecting element that are directly coupled to one another so that the drug and the solvent can be mixed after actuation of a passage valve.

A preset breakage point is furthermore provided that enables the connecting element to be separated from the container and from the receptacle after preparation of the solution. Subsequently the receptacle and the connecting element can be connected at the breaking point to a catheter dedicated to administering the drug to a patient.

The container and the connecting element can be covered completely by a casing, preferably a transparent or translucent casing, that has a preset separating line in the region of the preset breaking point.

The kit disclosed in DE-43 14 090 C2 is of limited use, as it is based mainly on a container in the shape of a syringe and a receptacle for the diluted drug. It has to be set up each time for each single use on the patient and cannot provide diluted drugs in a customised manner for each patient. Furthermore, it cannot use the drugs in the usual supplied packages.

Patent application EP-1 563 819 A1 presents a drip blender mixing apparatus for infusions that constitutes a safety system for patients and for medical personnel, with which medical accidents can be avoided in the preparation of infusions with drugs, for example antiblastic drugs.

The mixing apparatus for infusions comprises a unit for entering preset data that relate at least to the surface of the body of the patient, or the area under the curve (AUC) of the plasma-time concentration, or the bodyweight of the patient.

The apparatus furthermore comprises a calculating unit of the liquid to be supplied to determine the quantity of liquid drug or of diluted drug on the basis of the data entries; a guiding unit for inserting mixing tubes provided with channels for the liquid drug and for the diluted solution; supplying units of the liquid that are in contact respectively with the channel through which the drug passes and with the channel through which the diluted solution enters the mixing tube to be inserted into the guiding unit. The liquid drug or the solution are thus conveyed according to the required quantities, determined by the calculating unit.

The apparatus disclosed in EP-1 563 819 is rather complex, the calculating unit that defines the quantity of drug to be administered to the patient on the basis of the bodily parameters of the patient does not always ensure a correct calculation of the quantity of drug to be administered. Furthermore, the flow meters for controlling the quantities of drug being prepared do not always ensure safe and precise measuring.

Mixing and replacing components in contact with the drugs is complicated and there is no possibility of using normal packages of drugs such as those that are commercially available.

US 2005/0278066 A1 discloses an automated bulk dispensing system and a corresponding method of use, preferably intended for nuclear pharmaceuticals. The method comprises: selectively receiving a predetermined amount of radioactive liquid from a second container into a third container, selectively receiving a predetermined amount of nonradioactive liquid from a first container into a fourth container or directly into the third container, depending on whether kits or multi-dose containers of medicine are desired. The system further comprises: displacement mechanisms for mixing and dispensing liquid, which are connected to the third container and fourth container; at least one control valve, and preferably three control valves, which are each controlled by drive mechanisms; a gas vent and bubble detector for eliminating bubbles; a processor utilized to control the displacement mechanisms and the drive mechanisms.

An object of the invention is thus to improve known devices and methods for the dilution and preparation of antiblastic drugs.

Another object of the invention is to present a method and a device for the dilution and preparation of antiblastic drugs that are simple to make.

Another object of the invention is to present a method and a device for the dilution and preparation of antiblastic drugs in which the components in contact with the drugs can be easily replaceable and/or sterilisable.

Still another object is to present a method and a device that are accurate and precise in diluting and preparing drugs and which provide repeatable results.

In a first aspect of the invention there is provided a device for the dilution and preparation of an antiblastic drug as defined in claim 1.

In a second aspect of the invention, there is provided an apparatus for the dilution and preparation of an antiblastic drug comprising at least a drug preparation unit provided with a first central tank, in which there is a solvent, a first positive-displacement pump, for example a peristaltic pump, an emptying unit for at least a bottle of drug, the first positive-displacement pump being suitable for transferring in a dosed manner the solvent from the central tank to said at least a bottle of drug, a further tank for the semifinished drug that is filled by said positive-displacement pump subsequently to the bottle, wherein it comprises a first unit or replaceable main kit comprising a tip arrangement to be fitted onto the bottle of drug, the further tank for the semifinished drug and the connections of the various parts. From the second tank, through a second positive-displacement pump it will be possible to remove the right quantity of diluted drug.

Owing to the first and second aspect of the invention more simple management of antiblastic therapies is possible. Solutions of diluted drug can be obtained for the therapies using directly the bottles of drug in the various commercially available forms and dimensions. It is thus possible to administer therapies even with non-specialised staff, after short initial training.

Furthermore, all the components in contact with the antiblastic drugs can be easily replaced and/or sterilised.

The invention can be better understood and implemented with reference to the attached drawings, which illustrate an embodiment thereof by way of non-limitative example, in which.

Conceptually, the invention provides a device comprising at least a unit for the dilution and preparation of the antiblastic drug provided with a first central tank, in which there is a solvent, typically a physiological or glucosate solution, a first positive-displacement pump, for example a peristaltic pump, an emptying unit for at least a bottle of drug, and a further tank for collecting the diluted drug, i.e. semifinished drug.

The emptying unit fits into the bottle of drug with a tip system that is capable of perforating the cap in plastics, typically in ABS (acrylonitrile butadiene styrene). The first positive-displacement pump is used to transfer in a dosed manner the solvent from the central tank to at least a bottle of drug, by means of the emptying unit.

The bottle of the drug is lodged on a positioning and blocking system that is characterised by having a housing such as to be able to receive the various dimensions and various formats of bottle.

The emptying unit, provided with an inlet channel and an outlet channel, enables a further tank to be filled that will contain a solution with the dilution of the drug: this tank will be called tank of the semifinished drug. The inlet channel furthermore possesses two inlets both provided with nonreturn valves.

Through a second positive-displacement pump, the suitable dose of diluted drug is transferred from the tank of the semifinished drug to the container that will contain the final dilution of the antiblastic drug, i.e. the preparation. This container is set up for endovenous insertion.

There now follows a detailed description of the device and of the method that is the object of the invention.

Figure 1:
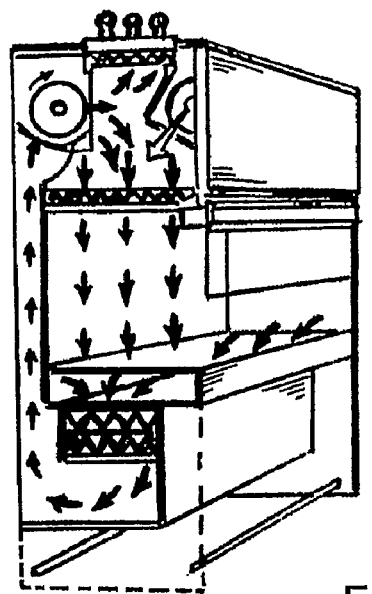
FIG. 1 illustrates a booth with class 11 vertical laminar flow hood currently used in the dilution and preparation of the antiblastic drugs.
Figure 2:
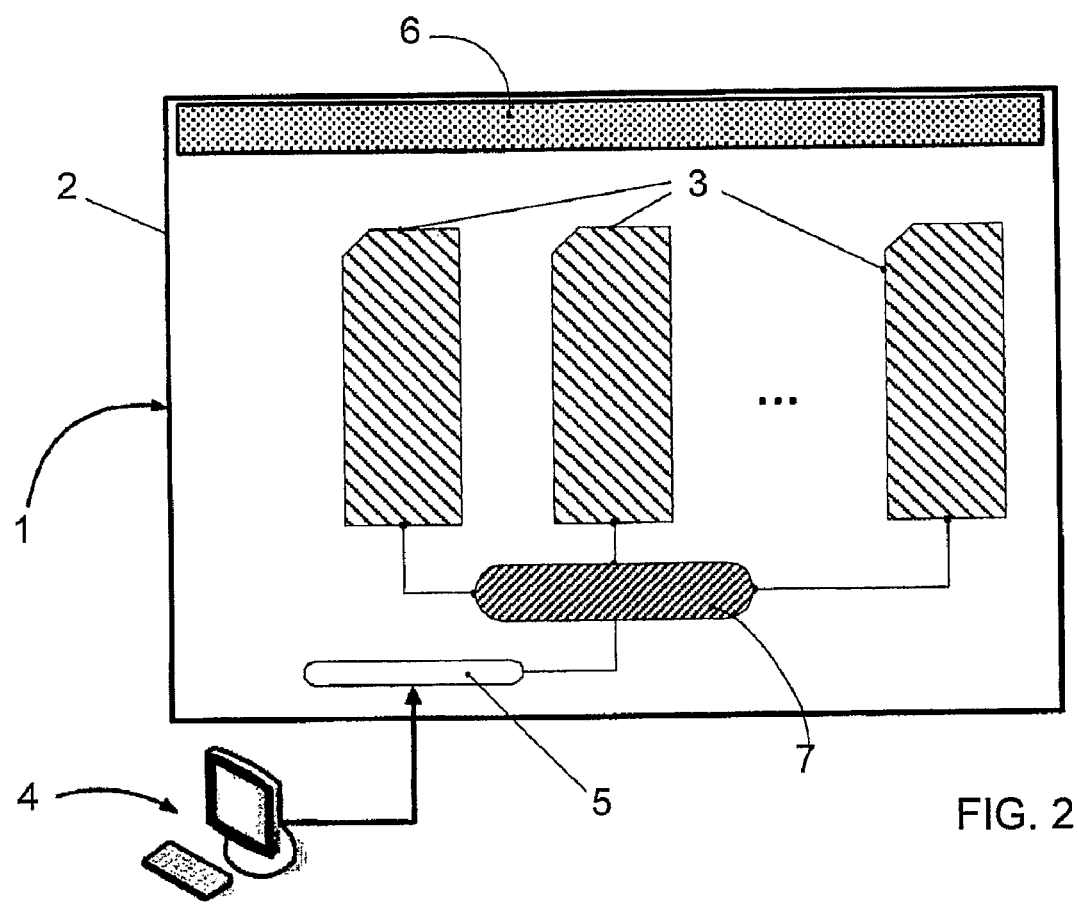
FIG. 2 is a block diagram of the device according to the invention.

According to what has been illustrated in FIG. 2, a device for the dilution and preparation of antiblastic drugs is indicated overall with 1 and comprises a casing 2, which contains a plurality of drug preparation units 3 that are independent and coordinated by a controlling device 4 through an electronic interface 5 connected to a controlling hardware 7 that guides the units 3 physically.

The drug preparation units 3 are connected electronically to the controller 7 by means of a rapid-type connector.

Each of the drug preparation units 3 treats one type of drug at a time individually and can generate the number of preparations that are necessary for a treatment session.

The presence of various drug preparation units 3 enables the device 1 to produce several preparations simultaneously, each made with different types of drug.

All the components that are inside the casing 2 are subject to the suction of a vertical laminar flow hood 6 to avoid contamination. All the processing area inside the device 1 is subject to continuous suction of the vapours generated, although these vapours are any way reduced to the minimum.

In the vertical laminar flow hood 6, the air is filtered through the HEPA-type hydrorepellent filter, i.e. a high-efficiency particulate filter that assures a sterile environment and that moves vertically from top to bottom, i.e. to the work area from which it is partially expelled and partially recirculated.

The vertical laminar flow produces sterilised external air suction, which creates a protective barrier against the external environment and at the same time prevents contamination of the area.

A conditioning arrangement can also be provided that is suitable for maintaining a constant temperature inside the device 1.

The controlling device 4 can be realised with any programmable device, for example: personal computers, palmtops, etc., in which data are managed by using one or more dedicated computer programme.

Through the computer programmes all the data are recorded that are necessary for preparing the treatment: patient's medical record, type of protocol used, sequence and dosage of drugs, administration cycles, etc.

It is also possible, when necessary, to request modifications to doses (typically a dose reduction).

In general, at least two types of programme exist, the first manages the device physically in the mechanical, hydraulic, pneumatic and electronic parts thereof, the second manages the data and the functions intended for the production of the preparation. In particular, the latter has to:

Manage the medical record of the patients of the treatment plans (protocols and supporting therapies): in this way the generating operations of the work schedule will be facilitated. The application thus has to enable customisation for the patient, automatically—by calculating the doses independently—and manually—if the oncologist deems a modification to be necessary (typically a dose reduction).

Manage the medical record of the patients in such a way as to automatically have information such as the body surface and eliminate calculation and/or transcription errors.

Generate the work schedule for the single patients, starting with the data in the treatment request: in this step the application will enable the patient to be associated with a basic protocol, adapting the patient thereto. In this context it will be possible to add supporting therapies and make percentage or numeric changes to the doses of the treatment.

Modify the information on the work schedule of the individual patient. The application enables the doses to be modified as percentages or by acting directly on the dose, enables pharmaceutical form, the type of administration and the time of administration, etc, to be modified. All the modifications can be made to the individual drug, to the single preparation, for the selected day or for the entire protocol.

View the state of the treatment.

Input notes by the oncologist.

Input notes for the administering personnel and/or view notes input by them during the administering step.

Compile statistics on the individual treatment protocols for the purposes of research and analysis, according to different criteria.

Compile statistics on consumption and cost, with forecasting of consumption.

Export data into the most common data formats: Text, Excel, xml.

Perform all the necessary printouts, in particular the work schedule of the day or of several days and the detail of administration, delivered to nursing staff together with the preparation: this sheet summarises the treatment of the patient, emphasising times and warnings (notes).

All the operations will have different levels of safety and access, as decided by the head of department.

The preparation unit 3 is illustrated in detail in FIGS. 3, 4, 5 and 6.

Figure 3:
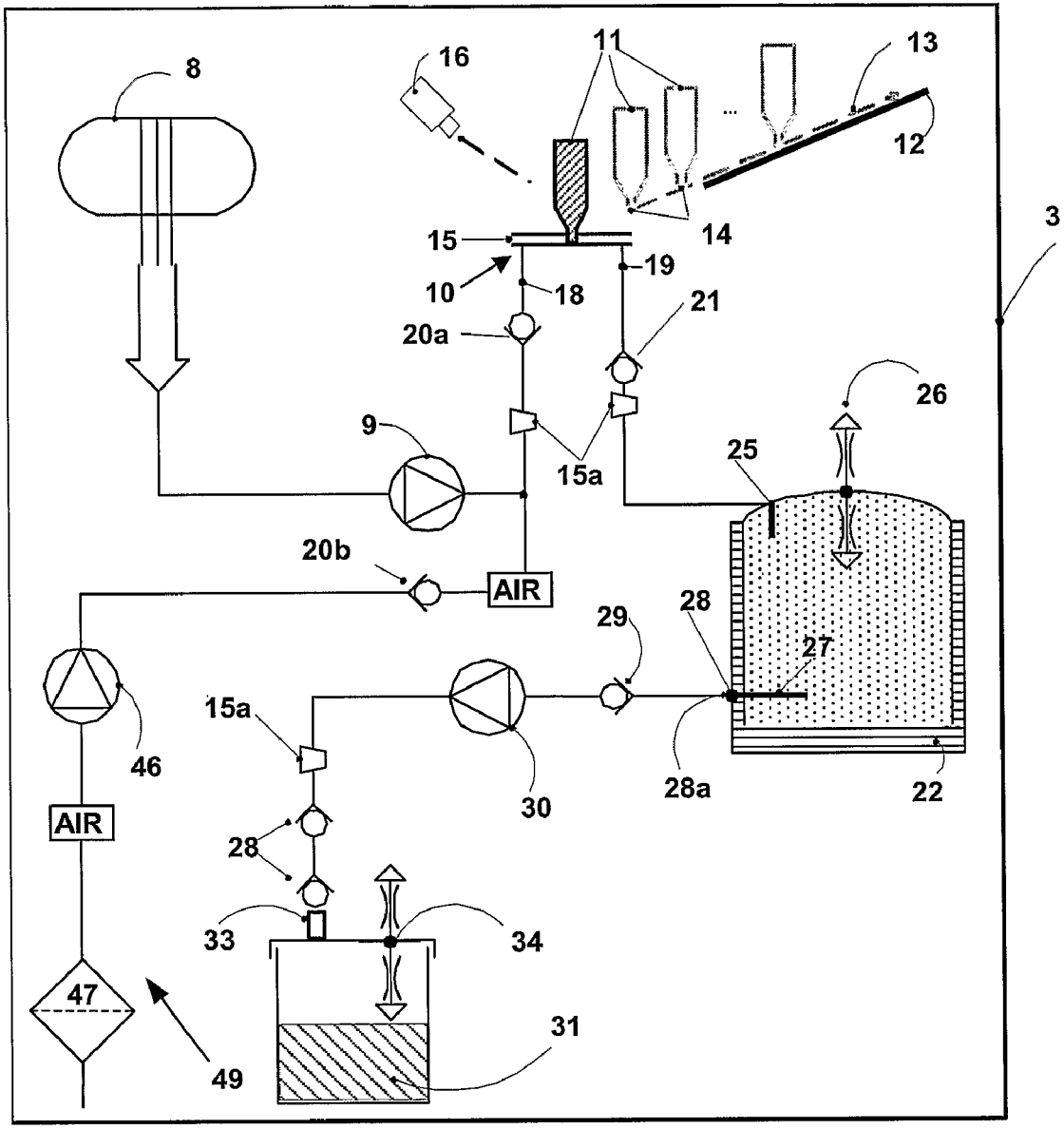
FIG. 3 illustrates a part of the device in an embodiment of the invention.
Figure 4:
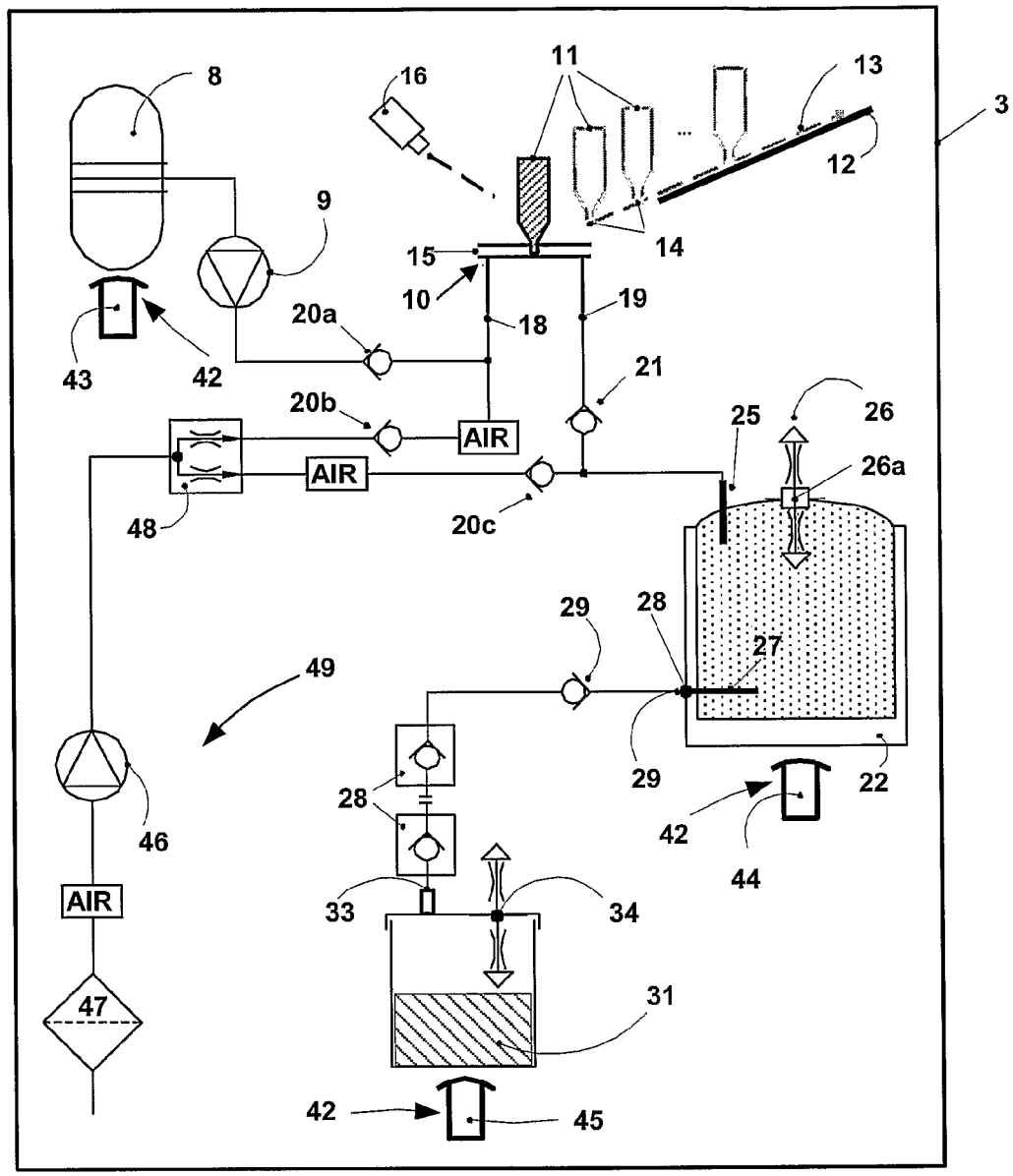
FIG. 4 illustrates a part of the device in a further embodiment of the invention.

According to FIGS. 3 and 4, the preparation unit 3 comprises a first central tank 8, in which there is a solvent, for example a physiological and/or glucosate solution, a first positive-displacement pump 9, for example a peristaltic pump, suitable for transferring the solution from the central tank 8 to an emptying unit 10 inserted automatically into a bottle of antiblastic drug 11.

The bottles of drug 11 are inside a magazine (not illustrated) that can also comprise a refrigerating zone.

The bottles of drug 11 are transferred using a loading arrangement 12 that comprises a dragging mechanism 13 and positioning and locking arrangement 14 for the bottles 11.

The dragging mechanism 13 is made according to one of the many methods available in the industrial field: for example by means of a conveyor belt.

As the commercially available drugs are distributed in various packages and formats, the positioning and locking arrangement 14 has a housing for accommodating the neck of the bottle 11; this housing has to be adaptable so that it can receive the various formats of the bottles.

By analysing the various packages that are currently commercially available, it follows that the necks of the bottles 11 have a diameter that varies from 8 mm to 18 mm.

The housing of the positioning and locking arrangement 14 enables the bottle to be arranged with the head pointing downwards and is sufficiently great to contain the various sizes of the different formats.

Each housing is located on the dragging mechanism 13.

Recognising the drug covers an important safety aspect as it prevents one drug being used instead of another. Also for this reason, a dedicated computer programme is provided that will have to have the availability of the database of the usable drugs, also recording all the format and dimension features.

This recognising, which may occur indifferently both during the loading step and during the movement of the bottle on the dragging mechanism 13, occurs through the recognising device 16 that identifies the identifying bar code of the drug and therefore also the information relating to the drug.

The recognising device 16 can be realised through optical reading device such as a CCD reader, or a camera, or other available identifying technologies such as RFID—Radio Frequency Identification elements.

The bottle 11 is locked at the neck by a locking system (not shown) formed by two 'V' forks arranged in an opposite manner.

The bottle 11 is carried above the emptying unit 10, which has a tip arrangement 15, said tip arrangement 15 is then inserted inside the bottle 11 and subsequently removed when the bottle 11 has been completely emptied of the drug, following the passage of the solvent.

Figure 7:
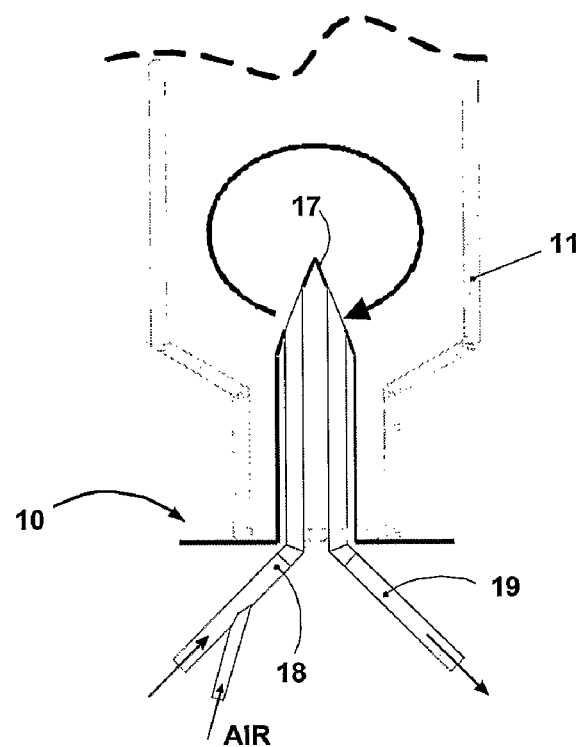
FIGS. 7-11 illustrate significant components of the device according to the invention.
Figure 8:
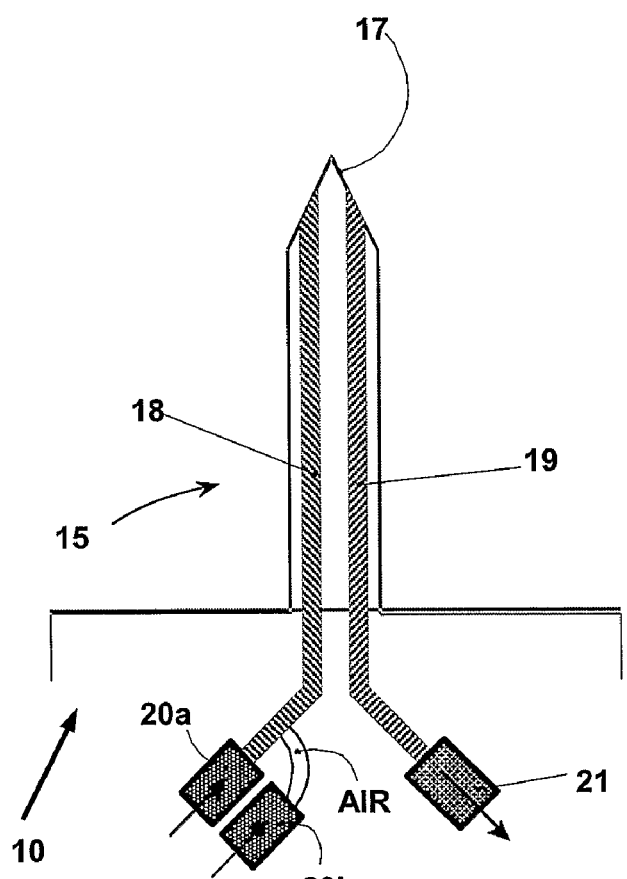

According to what is better illustrated in FIGS. 7 and 8, the emptying unit 10 comprises the tip arrangement 15, which comprises a tip 17 made of plastics. The material of the tip 17 has to be sufficiently hard to enable the cap of the bottle 11 to be perforated, considering that this cap is generally made of ABS (acrylonitrile butadiene styrene). The tip 17 can be made of various materials, for example any metal or plastic material. The material of the tip 17 has to be suitable and compatible for coming into contact with the drugs and the other solutions without altering them or creating reactions with the drugs.

In order to fill and empty the bottle of drug 11, the tip 17 comprises in turn a first inlet conduit 18, a second outlet conduit 19, a single-acting nonreturn valve 20a for solvent, a single-acting nonreturn valve 20b for filtered air, both the valves at the inlet to the bottle 11, and a single-acting nonreturn valve 21 at the outlet from the bottle 11. Through the valves 20a and 20b the various fluids can flow inside the bottle, i.e. the solvent from the part of the valve 20a and the filtered air from the part of the valve 20b.

The valves 20a, 20b and 21 can be made by means of a quickfit fitting 28 that will be disclosed in detail subsequently.

The first conduit 18 is connected to the central tank 8 containing the solvent.

The solvent is transfused inside the bottle 11 with an appropriate pressure value by means of the first positive-displacement pump 9. Once the bottle 11 has been filled, the solvent mixed with the drug will start to flow into the second outlet conduit 19 connected to a tank of the semifinished drug 22.

By supplying a suitable quantity of solvent, the bottle 11 will be completely emptied of the drug: at the end it will remain full of only solvent (with small margins of error).

Air-dispensing arrangement 49 can also be provided for the bottles 11, said arrangement 49 comprising a compressor, or a positive-displacement pump, for example a peristaltic pump 46, a filter 47 and a single-acting nonreturn valve 20b. Subsequently, the air-dispensing arrangement 49 delivers filtered air from the filter 47 through the single-acting nonreturn valve 20b in the conduit 18 of the emptying unit 10; this enables the bottle 11 to be emptied and cleaned also of the remaining solvent. This operation can be considered to be optional in the embodiment in FIG. 3.

At this point the bottle 11 is released in a suitable disposal container and a new bottle is fitted onto the emptying unit 10.

The antiblastic drugs are highly perishable once they have been opened, so they must be disposed of or used rapidly (typically within 24/48 hours).

The drugs are essentially distributed in two different states: in liquid state with various degrees of viscosity, and in lyophilised state, i.e. in powder.

The procedure adopted for dilution and preparation means that the result is independent of the physical state of the drug.

If the drug is in lyophilised state, the passage of the solvent inside the bottle provides for solubilisation thereof before use thereof.

This procedure is applied well also in cases in which use is made of bottles that have only 1 ml of solution, a quantity that would be unsuitable for flowing through a pipe of the hydraulic circuit (for example, for a pipe that is ⅛"—i.e. 3,175 mm—in diameter, 1 ml corresponds to about 3 linear cm): the losses would be unacceptable. The dilution process is thus an obligatory step before proceeding to the definitive transfer thereof.

Consequently, the tank of the semifinished drug 22 will fill up with diluted drug in known proportions.

As various preparations are produced from a bottle, one for each patient, several bottles might be necessary inside the same treatment session (typically a daily session) to generate all the necessary preparations.

For this reason, filling and emptying of the bottles of drug have to be repeated for a number of times so that inside the tank of the semifinished drug 22 there is the availability of diluted drug necessary for the producing all the preparations that will be used in the treatment session.

Figure 9:
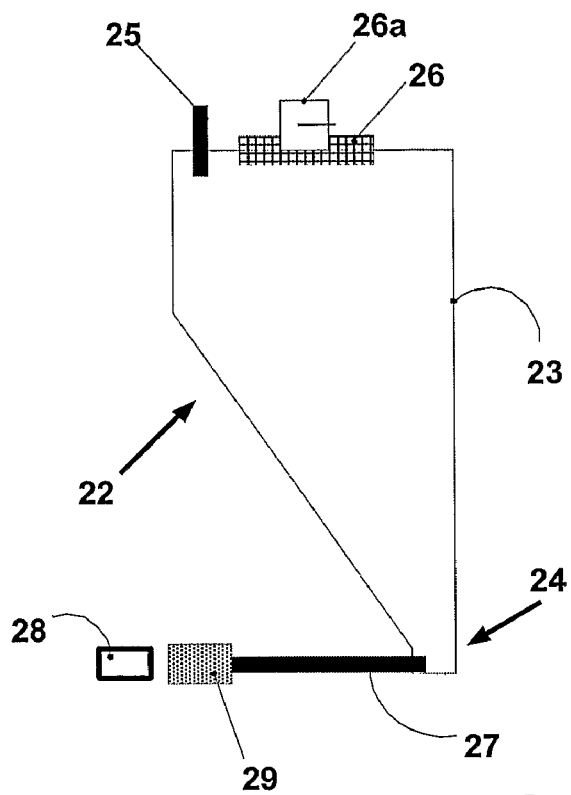

The tank of the semifinished drug 22 is illustrated in greater detail in FIG. 9.

The tank of the semifinished drug 22 comprises a casing 23 in non-transparent plastics and has an asymmetrical shape that tapers towards the bottom 24.

During emptying of the tank 22, this shape makes all the diluted drug converge on the bottom 24 so as to prevent there being zones of stagnation of the drug and so as to minimise losses.

In the upper part of the tank 22 there is an inlet conduit 25, connected to the second outlet conduit 19 of the emptying unit 10, and a hydrophobic filter 26 provided with an open/shut valve 26a (FIG. 4) that enables the tank to be ventilated, filtering particles and microorganisms. At the bottom 24 there is an outlet conduit 27 provided with a seat 28a intended to be associated with a quickfit fitting element 28.

The aforementioned quickfit fitting element 28 is of a special type for preventing losses of liquid during fitting and unfitting.

The conduit 27 is connected, by passing through the single-acting nonreturn valve 29 at the outlet from the tank 22, to bottles 31 that will contain the prepared drug. The function of the single-acting nonreturn valve 29 can be implemented in the quickfit fitting element 28, which also comprises a single-acting valve.

The diluted antiblastic drug is thus transferred from the tank of the semifinished drug 22 to a container 31 of prepared drug.

Figure 5:
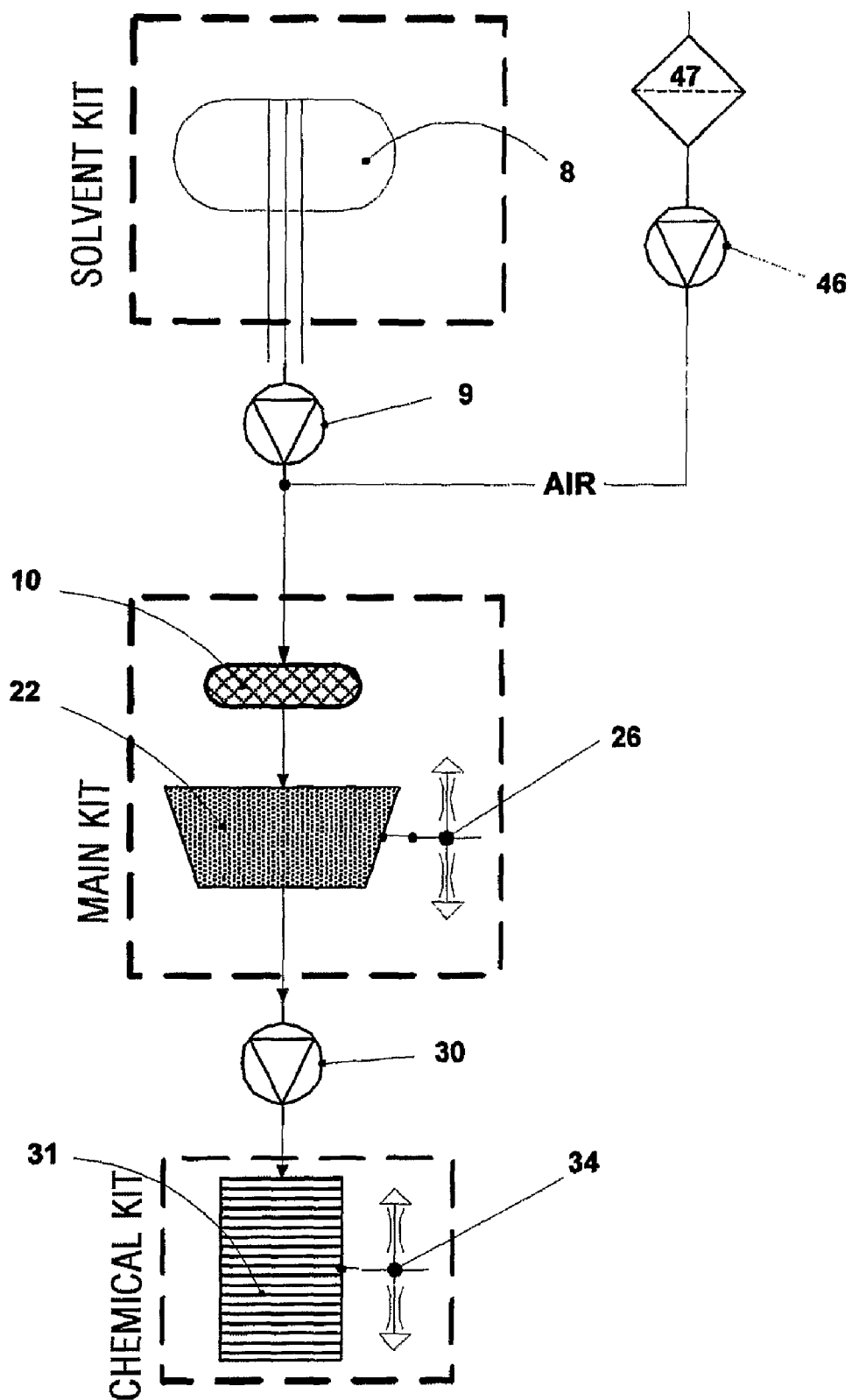
FIGS. 5 and 6 are block diagrams that illustrate schematically the parts of the device respectively in FIGS. 3 and 4.
Figure 6:
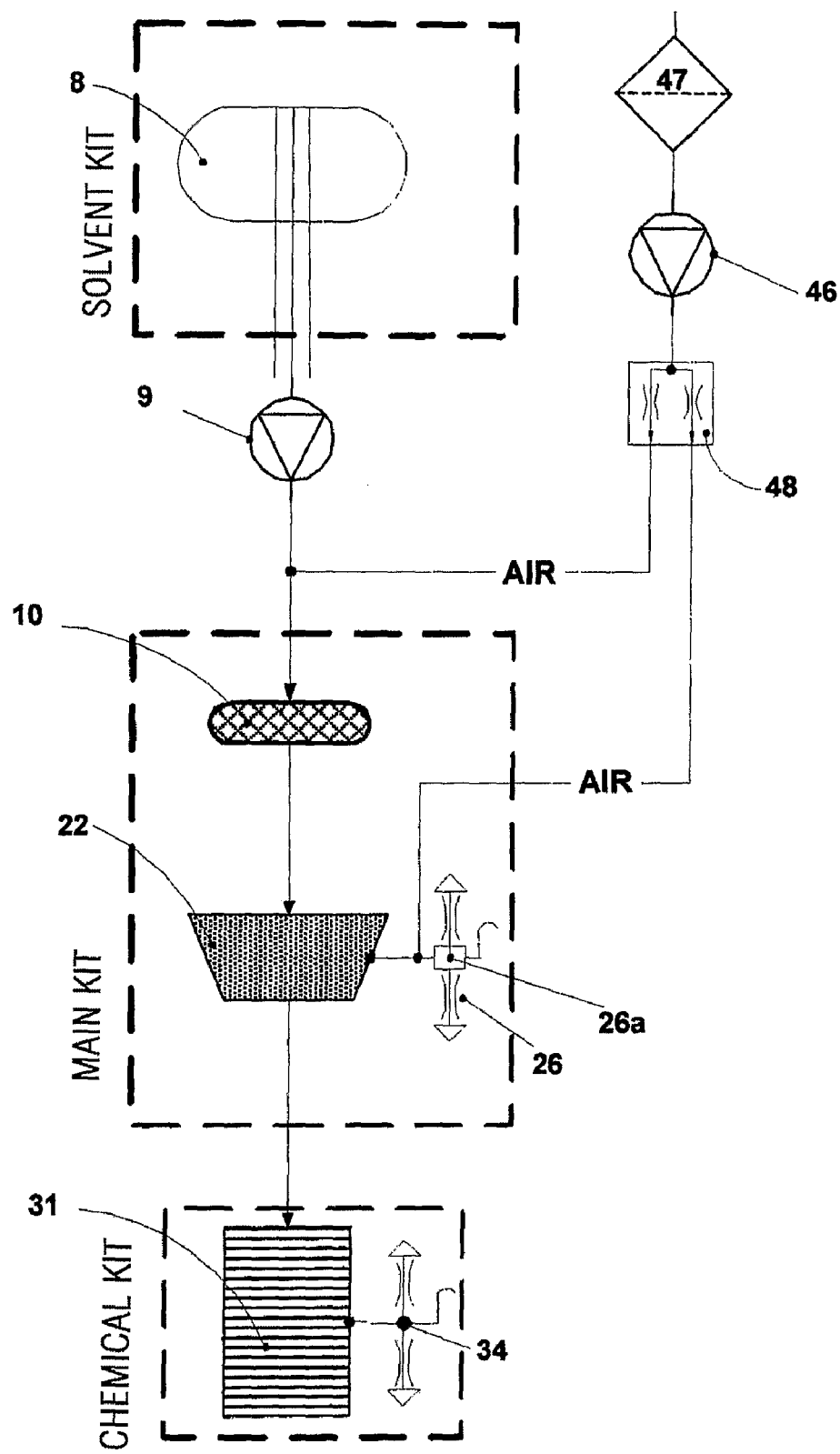

This may occur in two ways according to what is disclosed by the diagrams of FIGS. 3 and 4 and respectively of FIGS. 5 and 6.

In the version illustrated in FIGS. 3 and 5, a positive-displacement pump 30 is inserted between the tank 22 and the container 31 of prepared drug, the positive-displacement pump 30 removes the semifinished drug directly from the tank 22 and sends it to the container 31 in a dosed quantity. In the further version illustrated in FIGS. 4 and 6, the compressor, or the positive-displacement pump 46, pumps air inside the tank 22 through a single-acting nonreturn valve 20c, the air will push the contents of the tank 22 outside the conduit 27.

In the further version, the compressor, or the positive-displacement pump 46, is connected to a flow diverter 48, so as to send air in an exclusive manner to the valve 20b or to the valve 20c.

An example of embodiments for the compressors and for the positive-displacement pumps 9, 30 and 46 are provided by the peristaltic pump.

The main advantages of the peristaltic pump can be summarised as: no drawback in the event of dry operation; resistance of piping to most chemical products used; no seal loss; use of variable speeds and of different pipe diameters; possibility of operation in two opposite directions; facilitated cleaning because the liquid does not come into contact with mechanical parts; the only part that requires maintenance is the piping that in this case is of the disposable type (use-and-throw way); possibility of sterilising and cleaning inside the pump by means of disinfecting and/or sterilising arrangement.

In the version illustrated in FIG. 3, it should be noted that the positive displacement pumps 9 and 30, owing to the constructional features thereof, enable the exactly dosed quantities of liquid to be provided and do not require additional devices for checking the quantity of dispensed liquid.

It will nevertheless be necessary to apply flow sensors 15*a* outside the connecting pipes to indicate the start and the end of the passage of the liquid therein.

The controlling device 4 automatically calculates the quantity of drug that has to be introduced into the container 31 of the prepared drug, removing it from the tank of the semifinished drug 22 where the drug was already diluted previously.

In the further version illustrated in FIG. 4, below the first central tank 8, the tank of the semifinished drug 22 and the container of prepared drug 31 weight-detecting device 42 is placed made by means of the electronic devices 43, 44 and 45.

Each electronic device 43, 44 and 45 comprises sensors and transmitting arrangement for transmitting the signal able to detect and transmit the deformation to which they are subjected during the weighing operation in the form of an electric pulse that can be read by digital readers at a suitable resolution in terms of bits, an example of such a device is the load cell.

The transfer of the semifinished drug from the tank 22 to the container 31 occurs by automatically operating the closure of the valve 26*a* and pumping filtered air from the filter 37 to inside the tank 22, which through the difference of pressure exits from the conduit 27, filling the container 31. The controlling device 4 is able, by measuring the weight differences, to calculate automatically the quantity of drug that has to be introduced into the container 31 of the prepared drug.

In this case, the flow sensors 15*a* may be superfluous, but could represent a further controlling device. For safety reasons it is necessary to provide a detecting device for protecting the pressure in the tank of the semifinished drug 22 that can immediately arrest the process in the event of error.

Figure 10:
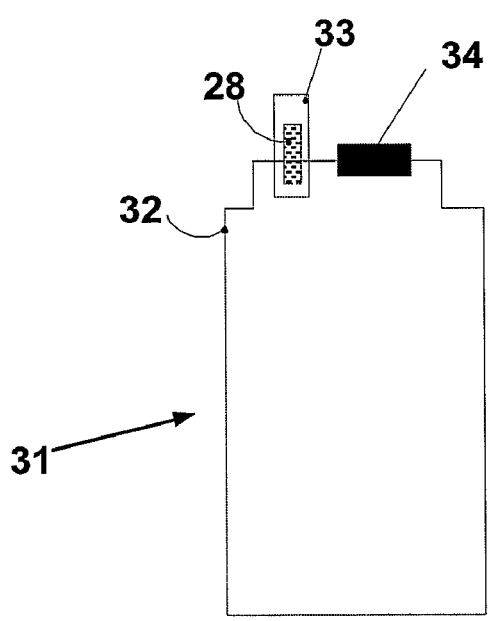

According to what has been illustrated in detail in FIG. 10, the container 31 comprises a casing 32 in non-transparent plastics and in the upper part comprises an inlet conduit 33, provided with un quickfit fitting 28, and a hydrophobic filter 34 that enables the container 31 to be ventilated, filtering particles and microorganisms.

The inlet conduit 33 of the container 31 is connected to the outlet conduit coming from the second positive-displacement pump 30.

At the end of the processing step of the prepared drug the preparation unit 3 can emit acoustic and/or visual signals that indicate to the operator that he has the possibility of extracting the container 31 with the drug, which is ready to be administered to the patient.

In the embodiment illustrated in FIG. 3 the steps of preparation of the semifinished drug and of transferring the drug to the container 31 can also occur parallel.

Figure 11:
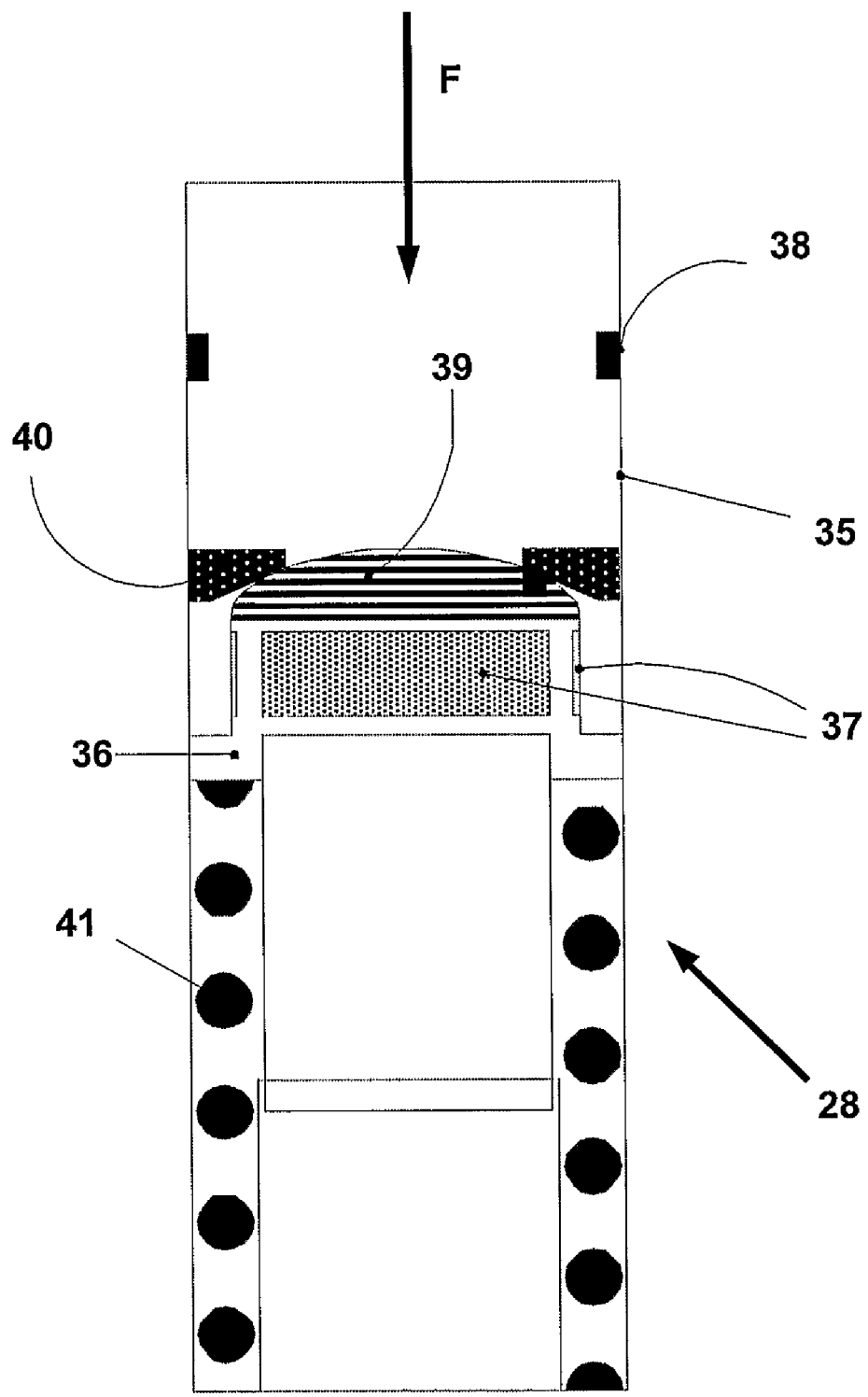

The quickfit fitting 28, illustrated in detail in FIG. 11, enables the passage of liquid in a direction indicated by F in the figure, and comprises a casing 35 intended to be inserted into a suitable seat 28*a*, for example a seat obtained in the tank 22, by means of a locking ring 38.

Inside the casing 35 there is a piston 36 provided with openings 37 suitable for permitting the passage of the liquid through the quickfit fitting. The piston 36 has a sealing head 39 that is normally kept closed on a seat 40 by means of a spring 41. All the components (connectors, valves, pipes and containers) that come into contact with the drug cannot be used with any other type of drug and, after preparation, will have to be replaced and disposed of or be washed and sterilised. In order to facilitate the replacement or the sterilisation of the above components, three disposable units or kits are used, that are illustrated in FIGS. 5 and 6: a first kit, said main kit, a second kit, said chemical kit and a third kit, said solvent kit.

The first unit or main kit comprises the emptying unit 10 to be fitted onto the bottle 11 of drug, the tank 22 for the semifinished drug and all the plastic elements for connecting the various parts.

The emptying unit 10 is integral with the tank of the semifinished drug 22 and is assembled industrially.

The kit is mounted inside the appropriate area of the device 3, hooking it onto suitable self-locking fittings (not shown) and inserting the flexible tube inside specific guides and inside the circuit of the peristaltic pump.

The tank of the semifinished drug 22 is subject to both the steps of loading and unloading, so it also has to comprise a ventilated valve 26, provided with a hydrophobic filter, for example a 0.22 micron ($\mu$m) hydrorepellent filter, which enables the tank 22 to be bled. In the embodiment illustrated in FIG. 4 the valve 26 has to be provided with a seal opening/closure.

The second unit or chemical kit, comprises the container 31 for the prepared drug. The container 31 is made of plastics that are opaque to light (for example polyethylene), can have any shape, for example a parallelpipedon shape, and comprises a cap provided with ventilated valve 34, provided with a hydrophobic filter, for example a 0.22 micron ($\mu$m) hydrorepellent filter that enables the container 31 to be bled.

This is also subject to both the steps of loading and unloading the prepared drug. The container 31 is provided with un quickfit fitting 28, that enables an easy connection both to a corresponding part of the main kit and to a flexible pipe that subsequently has to be connected, for example, to the infusion tubing used in endovenous administration.

On the faces of the container 31 there is present a writeable or printable surface that will be used to display at the end of the preparation of the drug the data necessary for identifying the preparation: the name of the drug, the dosage thereof, the name of the patient and the date of production and/or administration. The third unit or solvent kit comprises the central container 8 that contains the solvent (typically a physiological or glucosate solution).

The method for the dilution and preparation of antiblastic drugs comprises essentially the following steps:
    inputting into the controlling device 4 the chemotherapeutical protocol sheets, the data relating to the drugs, the data relating to the patients, etc.;
    loading and/or replacing manually the central tank 8, if empty (solvent kit);

removing the main unit or kit used in any preceding drug transferring step;

housing a new main unit or kit to be used in a new transferring step of the drug;

loading manually or automatically at least a bottle of drug 11 using the loading arrangement 12;

transferring in a dosed manner the solution coming from the central tank 8 to the bottle of drug 11 and then to the tank of the semifinished drug 22;

transferring in a dosed manner the diluted drug by removing it from the tank of the semifinished drug 22 and sending it to the container 31 of the prepared end drug;

removing the container 31 of the prepared drug, i.e. the end product, ready to be inserted endovenously into a patient;

removing the bottles and the containers 11, 22, 31 for disposal.

The device and the method according to the invention enable the known devices and methods for the dilution and preparation of antiblastic drugs to be improved.

In particular, the device and the method enable:

the chemotherapeutical protocol sheets of the patients (CPS) to be managed in a computerised manner the database of the drugs in the protocols, including all the data therein on the types of commercially available packaging to be managed automatically calculating the doses for the production of the bottles with the drug in solution automatically selecting the different types of drug necessary for the production of the preparations automatically receiving the different formats of bottles of drugs present treating indifferently drugs in different physical or liquid states (more or less viscous) and in powder (to be solubilised)

treating the drugs that have critical quantities, for example quantities up to 1 ml producing in complete safety customised doses, avoiding direct handling of the antiblastic drugs by humans making, in the correct conditions, several preparations simultaneously, unlike what happens now with the manual procedure printing in the appropriate space of the preparation container the essential identifying data such as the name of the drug, the dosage thereof, the name of the patient and the production/administration date presenting a series of automatic procedures for controlling and testing both the type of drugs used and the bottles produced optimising the choice of formats of the bottles of drug, to minimise residues having the components in contact with the antiblastic drugs easily replaceable and/or washable/sterilisable and/or of disposable type;

being able to be easily handled by non-specialised personnel after short initial training releasing the container for disposing of the special refuse automatically maintaining, optionally, a constant temperature inside the device.

the internal parts being easily accessible for washing and maintenance possessing, optionally, a refrigerating zone for storing drugs having the system entirely controlled by electronics and a dedicated management software having the software system easily updateable by the operators providing repeatable results.

The device according to the invention is able to receive the various formats of the commercially available bottles of drugs; it has modest dimensions and weight, so as to be able to be located anywhere easily; it has a series of automatic procedures for controlling and testing both the type of drugs used and the bottles produced; it is able to release the container for disposal of the special refuse automatically; owing to the constructional features, the internal parts are easily accessible, for washing and maintenance. The device according to the invention can make in the correct conditions several drug preparations simultaneously. In fact, the controlling device 4 is able to manage the chemotherapeutical protocol sheets of the patients, the database of the drugs permitted in the protocols and can store all the data on the commercially available packages relating to them. The device according to the invention automatically calculates the doses for the production of the bottles with the drug in solution; it requests the various types of drug necessary and can prepare in complete security customised doses for each patient, thus avoiding direct handling of the antiblastic drugs by humans.

The invention claimed is:

1. Device for the dilution and preparation of antiblastic drugs comprising at least one drug preparation unit provided with a first central tank, said first central tank containing a solvent, a first positive-displacement pump, said first positive-displacement pump comprising a peristaltic pump, an emptying unit for at least one bottle of drug, said first positive-displacement pump being suitable for transferring in a dosed manner said solvent from said central tank to said at least one bottle of drug, said emptying unit comprising a positioning and locking arrangement having a housing suitable for receiving various dimensions and formats of said bottles, wherein said device comprises a further tank for the semi-processed drug, said further tank being filled by said first positive-displacement pump after said at least one bottle of drug, a second positive-displacement pump, said second positive-displacement pump comprising a peristaltic pump, for transferring in a dosed manner the diluted drug from said further tank of the semi-finished drug to a container of prepared drug, wherein said further tank comprises in the upper part an inlet conduit and a hydrophobic filter that enables the tank to be ventilated, filtering particles and microorganisms.

2. Device according to claim 1, wherein said housing is suitable for receiving dimensions and formats of commercially available bottles containing antiblastic drugs.

3. Device according to claim 1, wherein said emptying unit comprises a first unit or replaceable main kit comprising a tip arrangement to be fitted to said bottle of drug, said further tank for the semiprocessed drug and pipes for connecting the various parts.

4. Device according to claim 3, wherein the tip arrangement comprises a tip that comprises in turn a first inlet conduit, a second outlet conduit.

5. Device according to claim 4, wherein the tip arrangement comprises a single-acting nonreturn valve at the inlet to said bottle and a single-acting nonreturn valve at the outlet from said bottle.

6. Device according to claim 1, comprising said container of drug prepared for a patient.

7. Device according to claim 1, comprising an air-dispensing arrangement suitable for delivering compressed air into said bottle of drug.

8. Device according to claim 7, wherein said air-dispensing arrangement comprises a compressor or a positive-displacement pump.

9. Device according to claim 7, wherein said air-dispensing arrangement comprises a filter suitable for filtering the air to be delivered into said bottle of drug.

10. Device according to claim 7, wherein said air-dispensing arrangement comprises a single-acting nonreturn valve that is suitable for permitting a flow of air to said bottle of drug.

11. Device according to claim 7, comprising a flow diverter suitable for diverting the airflow coming from said air-dispensing arrangement in an exclusive and alternative manner to said bottle of drug or to said tank of semifinished drug.

12. Device according to claim 11, comprising an air-supply conduit for said tank of semifinished drug provided with a single-acting nonreturn valve suitable for enabling an airflow to said tank of semifinished drug.

13. Device according to claim 11, comprising a weight-detecting device suitable for detecting the weight of the contents of at least said first central tank, or of said tank of the semifinished drug or of said container of prepared drug.

14. Device according to claim 13, wherein said weight-detecting device is applied to said first central tank, to said tank of the semifinished drug and to said container of prepared drug.

15. Device according to claim 13, wherein said weight-detecting device comprises sensors and a transmitting arrangement for transmitting the signal that is able to detect and transmit the deformation to which they are subjected during weighing operations.

16. Device according to claim 13, wherein said weight-detecting device comprises load cells.

17. Device according to claim 1, comprising a casing that contains at least one drug preparation unit.

18. Device according to claim 17, wherein said casing is provided with a laminar flow hood, so that all the components that are inside said casing are subject to the suction of said vertical laminar flow hood.

19. Device according to claim 1, comprising a controlling device for controlling and managing said at least one drug preparation unit.

20. Device according to claim 19, wherein said controlling device is realised with a programmable device, for example a personal computer, palmtop, etc.

21. Device according to claim 1, comprising a magazine inside which there are said bottles of drug.

22. Device according to claim 21, wherein said magazine comprises a refrigerating zone.

23. Device according to claim 1, comprising a recognising arrangement for identifying and recognising the identifying code of the drug and therefore identifying the information on the drug.

24. Device according to claim 1, wherein said drug preparation unit comprises a dragging mechanism for transferring said bottles.

25. Device according to claim 24, wherein said dragging mechanism comprises a conveyor belt.

26. Device according to claim 1, wherein said further tank comprises a further casing in plastic material that is not transparent to the light and has an asymmetrical and tapered shape towards the bottom.

27. Device according to claim 1, comprising a second unit, or replaceable chemical kit, consisting of said container for the prepared drug.

28. Device according to claim 1, comprising a third unit or replaceable kit container, consisting of said central tank filled with said solvent.

* * * * *